(12) United States Patent
Bernardeau et al.

(10) Patent No.: US 11,382,938 B2
(45) Date of Patent: Jul. 12, 2022

(54) BACILLUS-BASED COMPONENTS FOR INHIBITING OR DELAYING THE GROWTH OF ENTEROCOCCUS SPP. IN ANIMALS

(71) Applicant: DUPONT NUTRITION BIOSCIENCES APS, Copenhagen K (DK)

(72) Inventors: Marion Bernardeau, Caen (FR); Alexandra Wealleans, Wiltshire (GB)

(73) Assignee: DuPont Nutrition Biosciences APS, Copenhagen (DK)

( * ) Notice: Subject to any disclaimer, the term of this patent is extended or adjusted under 35 U.S.C. 154(b) by 0 days.

(21) Appl. No.: 16/464,569

(22) PCT Filed: Dec. 13, 2017

(86) PCT No.: PCT/US2017/066030
§ 371 (c)(1),
(2) Date: May 28, 2019

(87) PCT Pub. No.: WO2018/112006
PCT Pub. Date: Jun. 21, 2018

(65) Prior Publication Data
US 2021/0100850 A1    Apr. 8, 2021

Related U.S. Application Data

(60) Provisional application No. 62/435,214, filed on Dec. 16, 2016.

(51) Int. Cl.
*A61K 35/742* (2015.01)
*A23K 50/75* (2016.01)
*A23K 10/18* (2016.01)
*A61P 31/00* (2006.01)

(52) U.S. Cl.
CPC ............ *A61K 35/742* (2013.01); *A23K 10/18* (2016.05); *A23K 50/75* (2016.05); *A61P 31/00* (2018.01)

(58) Field of Classification Search
CPC ......... A23K 50/75; A23K 10/18; A61P 31/00; A61K 35/742
See application file for complete search history.

(56) References Cited

FOREIGN PATENT DOCUMENTS

| RU | 2440413 C1 | 1/2012 | |
|---|---|---|---|
| WO | 2007044968 A2 | 4/2007 | |
| WO | 2012110778 A2 | 8/2012 | |
| WO | 2013029013 A1 | 2/2013 | |
| WO | WO-2014151837 A1 * | 9/2014 | ........... A61K 35/742 |
| WO | 2017207372 A1 | 12/2017 | |

OTHER PUBLICATIONS

Kadaikunnan et al Ann Clin Microbiol Antimicrob. 2015; 14: 9 (Year: 2015).*
Lee et al Research In Veterinary Science, British Veterinary Association, vol. 91, No. 3, 2011 pages e87-e91 (Year: 2011).*
Waititu et al. Poultry Science 2014, vol. 93, pp. 625-635. (Year: 2014).*

(Continued)

*Primary Examiner* — Jana A Hines

(57) ABSTRACT

A method for Inhibiting or Delaying the Growth of *Enterococcus* spp. in Animals using at least one *Bacillus*-based component is disclosed herein.

12 Claims, 7 Drawing Sheets

Average growth inhibition of *Enterococcus cecorum* strains by Enviva® PRO strains

(56) References Cited

OTHER PUBLICATIONS

Wideman et al., Prophylactic administration of a combined prebiotic and probiotic, or therapeutic administration of enrofloxacin, to reduce the incidence of bacterial chondronecrosis with osteomyelitis in broilers, Poultry Science, vol. 94, No. 1, Jan. 20, 2015, pp. 25-36.
Wideman, Bacterial chondronecrosis with osteomyelitis and lameness in broilers: a review, Poultry Science, vol. 95. No. 2, Feb. 1, 2016, pp. 325-344.
Borst et al., Pathogenesis of Enterococcal Spondylitis Caused by Enterococcus cecorum in Broiler Chickens, Veterinary Pathology, vol. 54, No. 1, Aug. 20, 2016, pp. 61-73.
International Search Report and Written Opinion of the International Searching Authority, PCT/US2017/066030, dated Mar. 28, 2018, 15 pages.
Donskey, et al., Effect of oral Bacillus coagulans administration on the density of vancomycin-resistant enterococci in the stool of colonized mice, Letters in Applied Microbiology, Dec. 20, 2001, vol. 33, pp. 84-88.
From et al., Toxin-Producing Ability among *Bacillus* spp Outside the *Bacillus cereus* Group, Applied and Environmental Microbiology, Mar. 2005, vol. 71, No. 3, pp. 1178-1183.
Parkinson et al., A case of bovine mastitis caused by Bacillus cereus, New Zealand Veterinary Journal, vol. 47, No. 1, Apr. 27, 1998, pp. 151-152 (Abstract only).
Agerholm et al., Diagnostic studies of abortion in Danish dairy herds. Zentralbl Veterinarmed A. Dec. 1997;44 (9-10):551-8. (Abstract only).
Geeraerts, "Use of Bacillus amyloliquefaciens for Clostridium perfingens and Clostridium difficile associated disease". Ghent University, Faculty of Veterinary Medicine, Merelbeke, Belgium, Oct. 4, 2016, 223 pages.
"Safety and efficacy of Enviva(R) PRO 202 GT (Bacillus amyloliquefaciens PTA-6507, Bacillus amyloliquefaciens NRRL B-50013 and Bacillus amyloliquefaciens NRRL B-50104) for chickens for fattening, chickens reared for laying and minor poultry species for fattening and to point of lay", EFSA Journal, Oct. 26, 2016, vol. 14, No. 16, 4505, 13 pages.

* cited by examiner

Antimicrobial activity of the CFS of *Bacillus amyloliquefaciens* subsp. *plantarum* 15AP4, BS8 and 2084 against *Enterococcus gallinarum* VTT E-97776T expressed as % of inhibition at the exact end-point when the control pathogen curve reaches OD 0.4

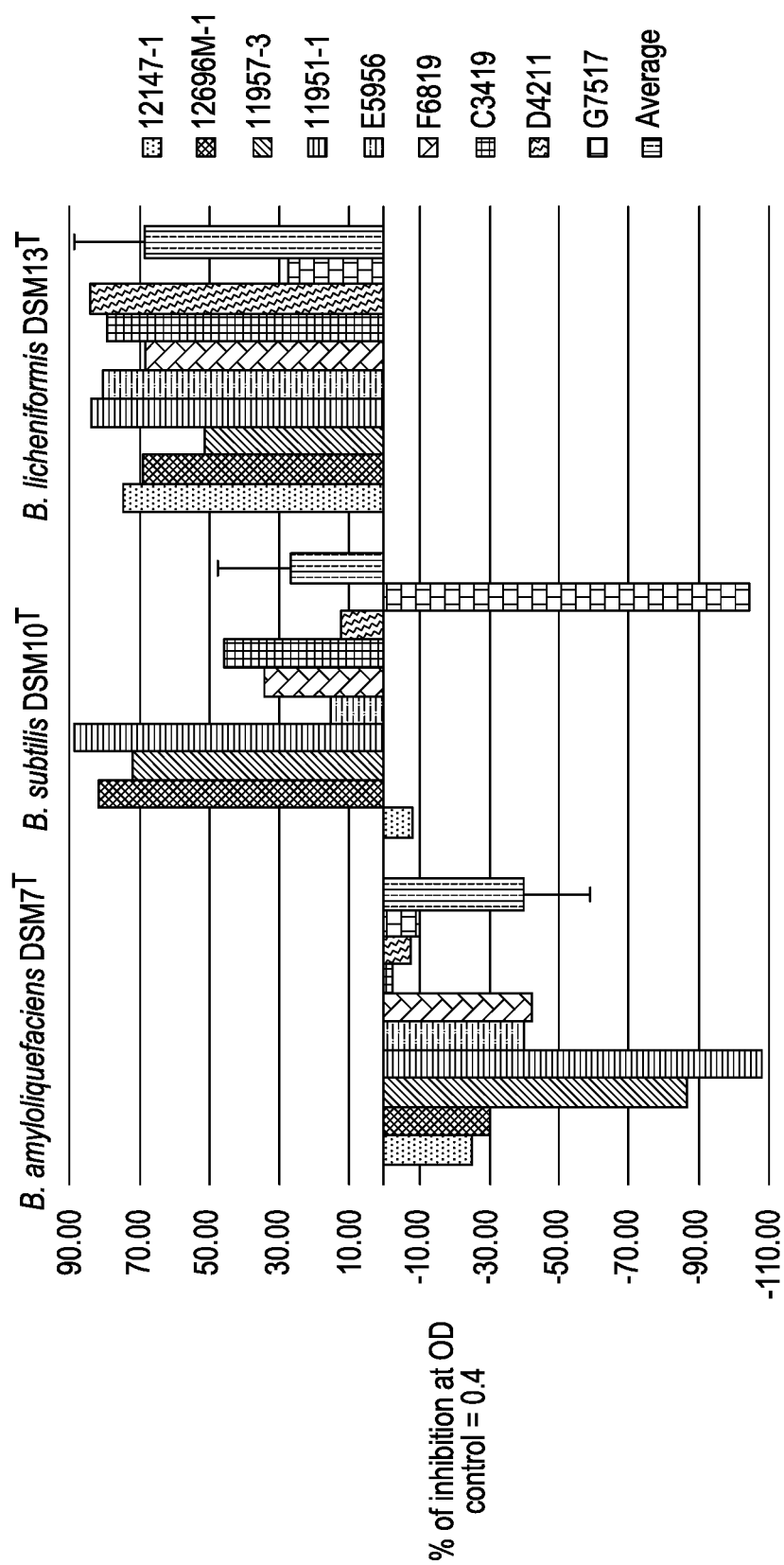

FIG. 7

Antimicrobial activity of the CFSs of *Bacillus amyloliquefaciens* DSM7$^T$, *B. subtilis* DSM10$^T$ and *B. licheniformis* DSM13$^T$ against 10 clinical isolates *Enterococcus cecorum* isolated from poultry production system in the US and in Belgium, expressed as % of inhibition at the exact end-point when the control pathogen curve reaches OD 0.4 (black bars correspond to the average % of inhibition)

BACILLUS-BASED COMPONENTS FOR INHIBITING OR DELAYING THE GROWTH OF ENTEROCOCCUS SPP. IN ANIMALS

CROSS-REFERENCE TO RELATED APPLICATIONS

The present application is a national stage entry under 35 U.S.C. § 371 of International Patent Application No. PCT/US2017/066030, filed Dec. 13, 2017, which, in turn, claims priority to U.S. Provisional Patent Application No. 62/435,241, filed Dec. 16, 2016, the disclosure of each of which is hereby incorporated by reference in its entirety.

FIELD

The field relates to the use of Bacillus-based components for inhibiting or delaying the growth of Enterococcus spp. in animals.

BACKGROUND

Enterococcus is a large genus of lactic acid bacteria of the phylum Firmicutes. Enterococci are Gram-positive cocci that often occur in pairs (diplococci) or short chains, and are difficult to distinguish from streptococci on physical characteristics alone. Enterococci are facultative anaerobic organisms, i.e., they are capable of cellular respiration in both oxygen-rich and oxygen-poor environments. Though they are not capable of forming spores, enterococci are tolerant of a wide range of environmental conditions: extreme temperature (10-45° C.), pH (4.5-10.0), and high sodium chloride concentrations. Members of the genus Enterococcus were classified as group D Streptococcus until 1984, when genomic DNA analysis indicated a separate genus classification would be appropriate. Among the Enterococcus species, some are known to be opportunistic pathogens when they get outside the gut. This is the case with respect to E. avium, E. gallinarum and E. cecorum, wherein E. cecorum is important in terms of economic losses sustained by poultry farmers in broiler chicken production chain.

Enterococcus cecorum is a normal inhabitant of the intestine of birds and other vertebrates such as horses, cattle, pigs, dogs, cats, canaries, pigeons, turkeys and Muscovy ducks. It is considered an emerging pathogen of poultry and other avian species. Femoral head necrosis and spondylitis have been described as the main pathological changes in infected chickens.

A part of the normal gut flora, disruptions or insult to normal gut function can result in Enterococcus cecorum translocation to the spine of birds. Enterococcus cecorum infections in the spine lead to vertebral and arthritic lesions, lameness and mortality in a condition known as enterococcal spondylothesis or "kinky back".

Spondylitis, referred to as "kinky back" by poultry producers, has been known in commercial production for many years and is typically seen in heavy, fast-growing birds, especially males and broiler breeders (Aziz, T. & Barnes, H. J. (2009). Spondylitis is emerging in broilers. World Poultry, 25, 19).

Highly pathogenic and antibiotic-resistant strains of Enterococcus cecorum continue to cause economic losses to the broiler chicken industry. Thus, routine farm hygiene procedures and antimicrobial therapy have proven insufficient to control outbreaks of pathogenic Enterococcus spp., especially, Enteroccocus cecorum.

Accordingly, a safe and efficacious alternative is needed to control this important emerging pathogen.

SUMMARY

In one embodiment, there is a disclosed a method for inhibiting or delaying all or part of the growth of pathogenic Enteroccocus spp. in an animal which comprises administering an effective amount of at least one Bacillus-based component selected from the group consisting of: a Bacillus-based direct fed microbial comprising one or more Bacillus bacterial strains, a supernatant obtained from a Bacillus culture or a combination thereof to an animal.

In a second embodiment, the Bacillus-based direct fed microbial is selected from the group consisting of Bacillus amyloliquefaciens, Bacillus licheniformis, Bacillus pumilis and Baccillus subtilis.

In a third embodiment, the Bacillus-based direct fed microbial is selected one or more of the following strains: Bacillus strain 2084 Accession No. NRR1B-50013, Bacillus strain LSSAO1 Accession No. NRRL B-50104 and Bacillus strain 15A-P4 ATCC Accession No. PTA-6507.

In a fourth embodiment, the animal can be a monogastric animal, preferably, can be poultry.

In a fifth embodiment, the animal can be a multigastric animal.

In a sixth embodiment, at least one Bacillus-based component can be administered directly to an animal through animal feed whether in the feed or on top of the feed or in a liquid such as water.

In a seventh embodiment, the Bacillus-based component can be administered to the animal in a form selected from the group consisting of a feedstuff, a feed additive composition, a premix or in a liquid such as water.

BRIEF DESCRIPTION OF THE DRAWINGS

FIG. 7 shows the antimicrobial activity of the CFSs of Bacillus amyloliquefaciens DSM7$^T$, B. subtilis DSM10$^T$ and B. licheniformis DSM13$^T$ against 10 clinical isolates Enterococcus cecorum, expressed as % of inhibition at the exact end-point when the control pathogen curve reaches OD 0.4.

DETAILED DESCRIPTION

Figure 1:
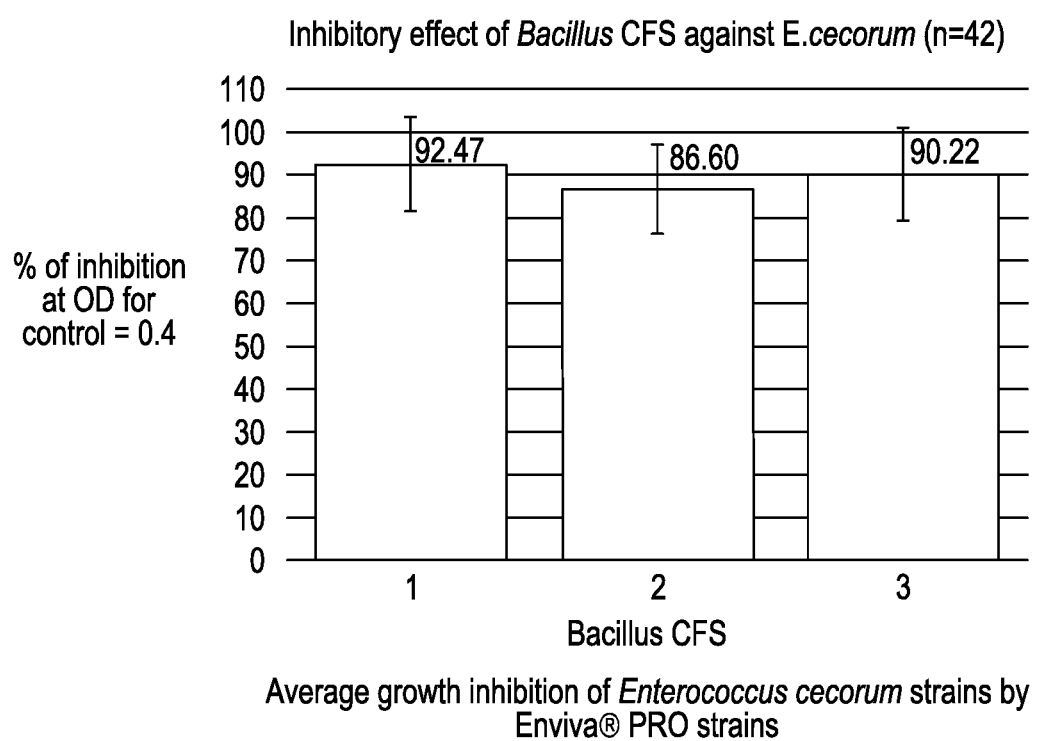
FIG. 1 shows the average inhibition for the E. cecorum strains collected from American and European poultry production by Enviva® PRO strains.

All patents, patent applications, and publications cited are incorporated herein by reference in their entirety.

In this disclosure, a number of terms and abbreviations are used. The following definitions apply unless specifically stated otherwise.

The articles "a", "an", and "the" preceding an element or component are intended to be nonrestrictive regarding the number of instances (i.e., occurrences) of the element or component. Therefore "a", "an", and "the" should be read to include one or at least one, and the singular word form of the element or component also includes the plural unless the number is obviously meant to be singular.

The term "comprising" means the presence of the stated features, integers, steps, or components as referred to in the claims, but that it does not preclude the presence or addition of one or more other features, integers, steps, components or groups thereof. The term "comprising" is intended to include embodiments encompassed by the terms "consisting essentially of" and "consisting of". Similarly, the term "consisting essentially of" is intended to include embodiments encompassed by the term "consisting of".

Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like.

As used herein in connection with a numerical value, the term "about" refers to a range of +/−0.5 of the numerical value, unless the term is otherwise specifically defined in context. For instance, the phrase a "pH value of about 6" refers to pH values of from 5.5 to 6.5, unless the pH value is specifically defined otherwise.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The terms "*Enterococcus*" and "*Enterococcus* spp." are used interchangeably and as used herein refers to a large genus of lactic acid bacteria of the phylum Firmicutes. Enterococci are Gram-positive cocci that often occur in pairs (diplococci) or short chains, and are difficult to distinguish from streptococci on physical characteristics alone. Enterococci are facultative anaerobic organisms, i.e., they are capable of cellular respiration in both oxygen-rich and oxygen-poor environments. Though they are not capable of forming spores, enterococci are tolerant of a wide range of environmental conditions: extreme temperature (10-45° C.), pH (4.5-10.0), and high sodium chloride concentrations. Members of the genus *Enterococcus* were classified as group D *Streptococcus* until 1984, when genomic DNA analysis indicated a separate genus classification would be appropriate.

The terms "*Enterococcus cecorum*" and "*E. cecorum*" are used interchangeably herein. *E. cecorum* is a species of *Enterococcus* and is a bacterium of the intestinal tract of many domestic animals.

The terms "animal" and "subject" are used interchangeably herein. An animal includes all non-ruminant (including humans) and ruminant animals. In a particular embodiment, the animal is a non-ruminant animal, such as a horse and a mono-gastric animal. Examples of mono-gastric animals include, but are not limited to, pigs and swine, such as piglets, growing pigs, sows; poultry such as turkeys, ducks, chicken, broiler chicks, layers; fish such as salmon, trout, tilapia, catfish and carps; and crustaceans such as shrimps and prawns. In a further embodiment, the animal can be multigastric, such as a ruminant animal, including, but not limited to, cattle, young calves, goats, sheep, giraffes, bison, moose, elk, yaks, water buffalo, deer, camels, alpacas, llamas, antelope, pronghorn and nilgai.

The term "ruminant" as used herein refers to a mammal that is able to acquire nutrients from plant-based food by fermenting it in a specialized stomach prior to digestion, principally, through microbial actions. The process typically requires the fermented ingesta (known as cud) to be regurgitated and chewed again. The process of rechewing the cud to further break down plant matter and stimulate digestion is called rumination. Roughly 150 species of ruminants include both domestic and wild species. Ruminating animals include, but are not limited to, cattle, cows, goats, sheep, giraffes, yaks, deer, elk, antelope, buffalo and the like.

The term "CFU" as used herein means "colony forming units" and is a measure of viable cells in which a colony represents an aggregate of cells derived from a single progenitor cell.

The term "direct-fed microbial" ("DFM") as used herein is source of live (viable) naturally occurring microorganisms. A DFM can comprise one or more of such naturally occurring microorganisms such as bacterial strains. Categories of DFMs include spore-forming bacteria such *Bacillus* and *Clostridium* as well non-spore forming bacteria such as Lactic Acid Bacteria, Yeasts and Fungi. Thus, the term DFM encompasses one or more of the following: direct fed bacteria, direct fed yeast, direct fed yeast or fungi and combinations thereof.

*Bacillus* and *Clostridium* are unique, gram-positive rods that form spores. These spores are very stable and can withstand environmental conditions such as heat, moisture and a range of pH. These spores germinate into active vegetative cells when ingested by an animal and can be used in meal and pelleted diets. Lactic Acid Bacteria are gram-positive cocci that produce lactic acid which are antagonistic to pathogens. Since Lactic Acid Bacteria appear to be somewhat heat-sensitive, they are not used in pelleted diets as such and need to be protected (coated). Types of Lactic Acid Bacteria include *Bifidobacterium, Lactobacillus* and *Enterococcus.*

The term "*Bacillus*-based direct-fed microbial" means a direct-fed microbial comprising one or more *Bacillus* bacterial strains.

The term "*Bacillus*-based component" as used herein refers to (i) a *Bacillus*-based direct fed microbial comprising one or more *Bacillus* bacterial strains, (ii) a supernatant obtained from a *Bacillus* culture or (iii) a combination of (i) and (ii).

A "feed" and a "food", respectively, means any natural or artificial diet, meal or the like or components of such meals intended or suitable for being eaten, taken in, digested, by a non-human animal and a human being, respectively.

As used herein, the term "food" is used in a broad sense—and covers food and food products for humans as well as food for non-human animals (i.e. a feed).

The term "feed" is used with reference to products that are fed to animals in the rearing of livestock. The terms "feed" and "animal feed" are used interchangeably. In a preferred embodiment, the food or feed is for consumption by non-ruminants and ruminants.

The term "probiotic" as used herein defines live microorganisms (including bacteria or yeasts for example) which, when for example ingested or locally applied in sufficient numbers, beneficially affects the host organism, i.e. by conferring one or more demonstrable health benefits on the host organism. Probiotics may improve the microbial balance in one or more mucosal surfaces. For example, the mucosal surface may be the intestine, the urinary tract, the respiratory tract or the skin. The term "probiotic" as used herein also encompasses live microorganisms that can stimulate the beneficial branches of the immune system and at the same time decrease the inflammatory reactions in a mucosal surface, for example the gut. Whilst there are no lower or upper limits for probiotic intake, it has been suggested that at least $10^6$-$10^{12}$, preferably at least $10^6$-$10^{10}$, preferably $10^8$-$10^9$, cfu as a daily dose will be effective to achieve the beneficial health effects in a subject.

The term "prebiotic" means a non-digestible food ingredient that beneficially affects the host by selectively stimulating the growth and/or the activity of one or a limited number of beneficial bacteria.

The term "pathogen" as used herein means any causative agent of disease. Such causative agents can include, but are not limited to, bacterial, viral, fungal causative agents and the like.

The terms "derived from" and "obtained from" refer to not only a protein produced or producible by a strain of the organism in question, but also a protein encoded by a DNA sequence isolated from such strain and produced in a host organism containing such DNA sequence. Additionally, the term refers to a protein which is encoded by a DNA sequence of synthetic and/or cDNA origin and which has the identifying characteristics of the protein in question.

The term "effective amount" means a sufficient amount of the specified component.

As was noted above, *Enteroccocus cecorum* is considered an emerging pathogen in poultry and can cause substantial losses in broiler and broiler breeder flocks. *E. cecorum* has been increasingly recognized as a cause of enterococcal spondylitis, previously called enterococcal vertebral osteoarthritis (EVOA) in chickens. Disease outbreaks were diagnosed mostly in broiler chicken flocks raised under an intensive production system. Clinically affected birds suffered from locomotor problems due to compression of the spinal cord at the thoracic vertebrae resulting from *E. cecorum*-induced osteomyelitis and due to femoral head necrosis. Disease outbreaks can lead to high morbidity, mortality, culling, carcass condemnations, and may result in severe economic losses within a short time. Furthermore, not only have isolates of *E. cecorum* have been demonstrating increased pathogenicity but also increased antimicrobial resistance.

Thus, the method described herein provides an alternative to the use of antibiotics since antimicrobial resistance is becoming a major global health threat.

In one embodiment, described herein is a method for inhibiting or delaying all or part of the growth of pathogenic *Enteroccocus* spp. in an animal which comprises administering an effective amount of at least one *Bacillus*-based component selected from the group consisting of: a *Bacillus*-based direct fed microbial comprising one or more *Bacillus* bacterial strains, a supernatant obtained from a *Bacillus* culture or a combination thereof to an animal.

The DFMs described herein comprise at least one viable microorganism such as a viable bacterial strain or a viable yeast or a viable fungus. Preferably, the DFM comprises at least one viable bacteria.

In one embodiment, the DFM may be a spore forming bacterial strain and hence the term DFM may be comprised of or contain spores, e.g. bacterial spores. Thus, the term "viable microorganism" as used herein may include microbial spores, such as endospores or conidia. Alternatively, the DFM in a feed additive composition described herein may not comprise of or may not contain microbial spores, e.g. endospores or conidia.

The microorganism may be a naturally-occurring microorganism or it may be a transformed microorganism. Preferably, the microorganism is a combination of at least three suitable microorganisms, such as bacteria, that may be isolated.

A DFM as described herein may comprise microorganisms from one or more of the following genera: *Lactobacillus*, *Lactococcus*, *Streptococcus*, *Bacillus*, *Pediococcus*, *Enterococcus*, *Leuconostoc*, *Carnobacterium*, *Propionibacterium*, *Bifidobacterium*, *Clostridium*, *Paenibacillus* and *Megasphaera* and combinations thereof.

Preferably, the DFM comprises one or more bacterial strains selected from the following *Bacillus* spp: *Bacillus subtilis*, *Bacillus amyloliquefaciens* and *Bacillus licheniformis*.

The genus "*Bacillus*", as used herein, includes all species within the genus "*Bacillus*", as known to those of skill in the art, including but not limited to *B. subtilis*, *B. licheniformis*, *B. lentus*, *B. brevis*, *B. stearothermophilus*, *B. alkalophilus*, *B. amyloliquefaciens*, *B. clausii*, *B. halodurans*, *B. megaterium*, *B. coagulans*, *B. circulans*, *B. gibsonii*, *B. pumilis* and *B. thuringiensis*. It is recognized that the genus *Bacillus* continues to undergo taxonomical reorganization. Thus, it is intended that the genus include species that have been reclassified, including but not limited to such organisms as *Bacillus stearothermophilus*, which is now named "*Geobacillus stearothermophilus*", or *Bacillus polymyxa*, which is now "*Paenibacillus polymyxa*". The production of resistant endospores under stressful environmental conditions is considered the defining feature of the genus *Bacillus*, although this characteristic also applies to the recently named *Alicyclobacillus*, *Amphibacillus*, *Aneurinibacillus*, *Anoxybacillus*, *Brevibacillus*, *Filobacillus*, *Gracilibacillus*, *Halobacillus*, *Paenibacillus*, *Salibacillus*, *Thermobacillus*, *Ureibacillus*, and *Virgibacillus*.

Preferably, the DFM may be one or more of the bacterial strains found in Enviva® PRO which is commercially available from Danisco A/S. Enviva° PRO is a combination of *Bacillus* strain 2084 Accession No. NRR1 B-50013, *Bacillus* strain LSSAO1 Accession No. NRRL B-50104 and *Bacillus* strain 15A-P4 ATCC Accession No. PTA-6507 (as taught in U.S. Pat. No. 7,754,469 B—incorporated herein by reference).

In another aspect, the DFM may be further combined with the following *Lactococcus* spp: *Lactococcus cremoris* and *Lactococcus lactis* and combinations thereof.

The DFM may be further combined with the following *Lactobacillus* spp: *Lactobacillus buchneri*, *Lactobacillus acidophilus*, *Lactobacillus casei*, *Lactobacillus kefiri*, *Lactobacillus bifidus*, *Lactobacillus brevis*, *Lactobacillus helveticus*, *Lactobacillus paracasei*, *Lactobacillus rhamnosus*, *Lactobacillus salivarius*, *Lactobacillus curvatus*, *Lactobacillus bulgaricus*, *Lactobacillus sakei*, *Lactobacillus reuteri*, *Lactobacillus fermentum*, *Lactobacillus farciminis*, *Lactobacillus lactis*, *Lactobacillus delbreuckii*, *Lactobacillus plantarum*, *Lactobacillus paraplantarum*, *Lactobacillus farciminis*, *Lactobacillus rhamnosus*, *Lactobacillus crispatus*, *Lactobacillus gasseri*, *Lactobacillus johnsonii* and *Lactobacillus jensenii*, *Lactobacillus acidophilus*, *Lactobacillus amylolyticus*, *Lactobacillus amylovorus*, *Lactobacillus alimentarius*, *Lactobacillus aviaries*, *Lactobacillus brevis*, *Lactobacillus buchneri*, *Lactobacillus casei*, *Lactobacillus*

*crispatus, Lactobacillus curvatus, Lactobacillus delbrueckii, Lactobacillus farciminis, Lactobacillus fermentum, Lactobacillus gallinarum, Lactobacillus gasseri, Lactobacillus helveticus, Lactobacillus hilgardii, Lactobacillus johnsonii, Lactobacillus kefiranofaciens, Lactobacillus kefiri, Lactobacillus mucosae, Lactobacillus panis, Lactobacillus paracasei, Lactobacillus paraplantarum, Lactobacillus pentosus, Lactobacillus plantarum, Lactobacillus pontis, Lactobacillus reuteri, Lactobacillus rhamnosus, Lactobacillus sakei, Lactobacillus salivarius, Lactobacillus sanfranciscensis, Lactobacillus zeae* and combinations of any thereof.

In still another aspect, the DFM may be further combined with the following *Bifidobacteria* spp: *Bifidobacterium lactis, Bifidobacterium bifidium, Bifidobacterium longum, Bifidobacterium animalis, Bifidobacterium breve, Bifidobacterium infantis, Bifidobacterium catenulatum, Bifidobacterium pseudocatenulatum, Bifidobacterium adolescentis*, and *Bifidobacterium angulatum*, and combinations of any thereof.

There can be mentioned bacteria of the following species: *Bacillus subtilis, Bacillus licheniformis, Bacillus amyloliquefaciens, Bacillus pumilis, Enterococcus, Enterococcus* spp., and *Pediococcus* spp, *Lactobacillus* spp., *Bifidobacterium* spp., *Lactobacillus acidophilus, Pediococcus acidilactici, Lactococcus lactis, Bifidobacterium bifidum, Bacillus subtilis, Propionibacterium thoenii, Lactobacillus farciminis, Lactobacillus rhamnosus, Megasphaera elsdenii, Clostridium butyricum, Bifidobacterium animalis* ssp. *animalis, Lactobacillus reuteri, Bacillus cereus, Lactobacillus salivarius* ssp. *Salivarius, Propionibacteria* sp and combinations thereof.

The direct-fed microbial described herein comprising one or more bacterial strains may be of the same type (genus, species and strain) or may comprise a mixture of genera, species and/or strains. Preferably, direct-fed microbial described herein comprising one or more bacterial strains from the genus *Bacillus*.

Suitably the composition according to the present disclosure may be combined with one or more of the products or the microorganisms contained in those products disclosed in WO2012110778, and summarized as follows:

*Bacillus subtilis* strain 2084 Accession No. NRR1 B-50013, *Bacillus subtilis* strain LSSAO1 Accession No. NRRL B-50104, and *Bacillus subtilis* strain 15A-P4 ATCC Accession No. PTA-6507 (from Enviva® PRO®. (formerly known as Avicor®); *Bacillus subtilis* Strain C3102 (from Calsporin®); *Bacillus subtilis* Strain PB6 (from Clostat®); *Bacillus pumilis* (8G-134); *Enterococcus* NCIMB 10415 (SF68) (from Cylactin®); *Bacillus subtilis* Strain C3102 (from Gallipro® & GalliproMax®); *Bacillus licheniformis* (from Gallipro® Tect®); *Enterococcus faeciul, Lactobacillus salivarius, L. reuteri, Bifidobacterium animalis* and *Pediococcus acidilactici* (from Poultry Star®); *Lactobacillus, Bifidobacterium* and/or *Enterococcus* from Protexin®); *Bacillus subtilis* strain QST 713 (from Proflora®); *Bacillus amyloliquefaciens* CECT-5940 (from Ecobiol® & Ecobiol® Plus); *Enterococcus faecium* SF68 (from Fortiflora®); *Bacillus subtilis* and *Bacillus licheniformis* (from BioPlus2B®); Lactic acid bacteria 7 *Enterococcus faecium* (from Lactiferm®); *Bacillus* strain (from CSI®); *Saccharomyces cerevisiae* (from Yea-Sacc®); *Enterococcus* (from Biomin IMB52®); *Pediococcus acidilactici, Enterococcus, Bifidobacterium animalis* ssp. *animalis, Lactobacillus reuteri, Lactobacillus salivarius* ssp. *salivarius* (from Biomin C5®); *Lactobacillus farciminis* (from Biacton®); *Enterococcus* (from Oralin E1707®); *Enterococcus* (2 strains), *Lactococcus lactis* DSM 1103(from Probios-pioneer PDFM®); *Lactobacillus rhamnosus* and *Lactobacillus farciminis* (from Sorbiflore®); *Bacillus subtilis* (from Animavit®); *Enterococcus* (from Bonvital®); *Saccharomyces cerevisiae* (from Levucell SB 20®); *Saccharomyces cerevisiae* (from Levucell SC 0 & SC10® ME); *Pediococcus acidilacti* (from Bactocell); *Saccharomyces cerevisiae* (from ActiSaf® (formerly BioSaf®)); *Saccharomyces cerevisiae* NCYC Sc47 (from Actisaf® SC47); *Clostridium butyricum* (from Miya-Gold®); *Enterococcus* (from Fecinor and Fecinor Plus®); *Saccharomyces cerevisiae* NCYC R-625 (from InteSwine®); *Saccharomyces cerevisia* (from BioSprint®); *Enterococcus* and *Lactobacillus rhamnosus* (from Provita®); *Bacillus subtilis* and *Aspergillus oryzae* (from Pep SoyGen-C®); *Bacillus cereus* (from Toyocerin®); *Bacillus cereus* var. *toyoi* NCIMB 40112/CNCM 1-1012 (from TOYOCERIN®), *Lactobacillus plantarum* (from LactoPlan®) or other DFMs such as *Bacillus licheniformis* and *Bacillus subtilis* (from BioPlus® YC) and *Bacillus subtilis* (from GalliPro®).

It is also possible to combine the DFM described herein with a yeast from the genera and species: *Debaryomyces hansenii, Hanseniaspora uvarum, Kluyveromyces lactis, Kluyveromyces marxianus, Pichia angusta, Pichia anomala, Saccharomyces bayanus, Saccharomyces cerevisiae, Saccharomyces pastorianus* (synonym of *Saccharomyces carlsbergensis*) and filamentus fungi from the genus *Aspergillus*.

Preferably, the DFM described herein comprises microorganisms which are generally recognized as safe (GRAS) and, preferably are GRAS-approved and/or Qualified Presumption of Safety by the European Food Safety Authority (EFSA)

In some embodiments, it is important that the DFM be heat tolerant, i.e., is thermotolerant. This is particularly the case when the feed is pelleted. Thus, the DFM may be a thermotolerant microorganism, such as a thermotolerant bacteria, e.g., spore-forming bacteria including for example *Bacillus* spp. Bacilli are able to form stable endospores when conditions for growth are unfavorable and are very resistant to heat, pH, moisture and disinfectants. If the bacterium/DFM is not a spore-former then it should be protected to survive feed processing as is described hereinbelow.

The *Bacillus*-based DFM as described herein described herein may inhibit or delay all or part of the growth of *Enterococcus* spp., e.g., *E. cecorum*. In other words, a *Bacillus*-based DFM as described herein is antipathogenic. The term "antipathogenic" as used herein means the DFM counters an effect (negative effect) of a pathogen, in this case, pathogenic *Enterococcus* spp., e.g., *E. cecorum*.

For example, the following assay "DFM ASSAY" may be used to determine the suitability of a microorganism to be a DFM or in this embodiment, a *Bacillus*-based DFM as described herein. Such DFM can be run as follows:

The fully grown culture of a *Bacillus* strain was centrifuged and filter-sterilized (0.2 µm) so as to obtain sterile cell free supernatant (CFS). Each well of a 96-well microtiter plate is filled with 180 µl of a pathogen/BHI (or appropriate growth media) suspension (1%). The positive control wells are filled with extra 20 µl of the same broth media whereas the tested wells are filled with 20 µl of the tested CFSs. The negative controls contain the broth media only or broth media added with 20 µl of CFS. The 96-well microtiter plate is then incubated aerobically at 37° C. for 14 hours in a Flex station machine to record absorbance, with data transferred directly to a computer for analysis so as to generate kinetics growth curve. Measurements were taken every 15 minutes. Results are given as % of inhibition comparing control at OD=0.4 (pathogen alone) and treated (pathogen incubated with Bacillus CFS). Delay in growth is calculated as the difference in time to reach OD 0.4 between control and CFS-supplemented wells. All assays are conducted in duplicate. Means separation was conducted using Tukey's HSD in AV 11; differences were considered significant at P<0.05.

Antipathogenic DFMs include one or more of the following bacteria and are described in WO2013029013:

Bacillus subtilis strain 3BP5 Accession No. NRRL B-50510,

Bacillus subtilis strain 918 ATCC Accession No. NRRL B-50508, and

Bacillus subtilis strain 1013 ATCC Accession No. NRRL B-50509.

A Bacillus-based component as described herein may be prepared as culture(s) and carrier(s) (where used) and can be added to a ribbon or paddle mixer and mixed for about 15 minutes, although the timing can be increased or decreased. The components are blended such that a uniform mixture of the cultures and carriers result. The final product is preferably a dry, flowable powder. Accordingly, a Bacillus-based component can comprise a: a Bacillus-based direct fed microbial comprising one or more Bacillus bacterial strains, a supernatant obtained from a Bacillus culture or a combination. Such a Bacillus-based component can then be added to animal feed or a feed premix. It can be added to the top of the animal feed ("top feeding") or it can be added to a liquid such as the animal's drinking water.

Inclusion of the individual strains in the Bacillus-based DFM as described herein can be in proportions varying from 1% to 99% and, preferably, from 25% to 75%.

Suitable dosages of the Bacillus-based component as described herein in animal feed may range from about $1\times10^3$ CFU/g feed to about $1\times10^{10}$ CFU/g feed, suitably between about $1\times10^4$ CFU/g feed to about $1\times10^8$ CFU/g feed, suitably between about $7.5\times10^4$ CFU/g feed to about $1\times10^7$ CFU/g feed.

A person of ordinary skill in the art will readily be aware of specific species and/or strains of microorganisms from within the genera described herein which are used in the food and/or agricultural industries and which are generally considered suitable for animal consumption. Animal feeds may include plant material such as corn, wheat, sorghum, soybean, canola, sunflower or mixtures of any of these plant materials or plant protein sources for poultry, pigs, ruminants, aquaculture and pets.

The terms "animal feed", "feed", and "feedstuff" are used interchangeably and can comprise one or more feed materials selected from the group comprising a) cereals, such as small grains (e.g., wheat, barley, rye, oats and combinations thereof) and/or large grains such as maize or sorghum; b) by products from cereals, such as corn gluten meal, Distillers Dried Grains with Solubles (DDGS) (particularly corn based Distillers Dried Grains with Solubles (cDDGS), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; and/or e) minerals and vitamins.

When used as, or in the preparation of, a feed, such as functional feed, a Bacillus-based component as described herein may be used in conjunction with one or more of: a nutritionally acceptable carrier, a nutritionally acceptable diluent, a nutritionally acceptable excipient, a nutritionally acceptable adjuvant, a nutritionally active ingredient. For example, there could be mentioned at least one component selected from the group consisting of a protein, a peptide, sucrose, lactose, sorbitol, glycerol, propylene glycol, sodium chloride, sodium sulfate, sodium acetate, sodium citrate, sodium formate, sodium sorbate, potassium chloride, potassium sulfate, potassium acetate, potassium citrate, potassium formate, potassium acetate, potassium sorbate, magnesium chloride, magnesium sulfate, magnesium acetate, magnesium citrate, magnesium formate, magnesium sorbate, sodium metabisulfite, methyl paraben and propyl paraben.

In a preferred embodiment, a Bacillus-based component as described herein may be admixed with a feed component to form a feedstuff. The term "feed component" as used herein means all or part of the feedstuff. Part of the feedstuff may mean one constituent of the feedstuff or more than one constituent of the feedstuff, e.g. 2 or 3 or 4 or more. In one embodiment the term "feed component" encompasses a premix or premix constituents. Preferably, the feed may be a fodder, or a premix thereof, a compound feed, or a premix thereof. A feed additive composition comprising a Bacillus-based component as described herein may be admixed with a compound feed or to a premix of a compound feed or to a fodder, a fodder component, or a premix of a fodder.

The term fodder as used herein means any food which is provided to an animal (rather than the animal having to forage for it themselves). Fodder encompasses plants that have been cut.

The term fodder includes hay, straw, silage, compressed and pelleted feeds, oils and mixed rations, and also sprouted grains and legumes.

Fodder may be obtained from one or more of the plants selected from: alfalfa (lucerne), barley, birdsfoot trefoil, brassicas, Chau moellier, kale, rapeseed (canola), rutabaga (swede), turnip, clover, alsike clover, red clover, subterranean clover, white clover, grass, false oat grass, fescue, Bermuda grass, brome, heath grass, meadow grasses (from naturally mixed grassland swards, orchard grass, rye grass, Timothy-grass, corn (maize), millet, oats, sorghum, soybeans, trees (pollard tree shoots for tree-hay), wheat, and legumes.

The term "compound feed" means a commercial feed in the form of a meal, a pellet, nuts, cake or a crumble. Compound feeds may be blended from various raw materials and additives. These blends are formulated according to the specific requirements of the target animal.

Compound feeds can be complete feeds that provide all the daily required nutrients, concentrates that provide a part of the ration (protein, energy) or supplements that only provide additional micronutrients, such as minerals and vitamins.

The main ingredients used in compound feed are the feed grains, which include corn, soybeans, sorghum, oats, and barley.

Suitably a premix as referred to herein may be a composition composed of microingredients such as vitamins, minerals, chemical preservatives, antibiotics, fermentation products, and other essential ingredients. Premixes are usually compositions suitable for blending into commercial rations.

Any feedstuff described herein may comprise one or more feed materials selected from the group comprising a) cereals, such as small grains (e.g., wheat, barley, rye, oats and combinations thereof) and/or large grains such as maize or sorghum; b) by products from cereals, such as corn gluten meal, Distillers Dried Grain Solubles (DDGS), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; e) minerals and vitamins.

Furthermore, such feedstuff may contain at least 30%, at least 40%, at least 50% or at least 60% by weight corn and soybean meal or corn and full fat soy, or wheat meal or sunflower meal.

In addition, or in the alternative, a feedstuff may comprise at least one high fibre feed material and/or at least one by-product of the at least one high fibre feed material to provide a high fibre feedstuff. Examples of high fibre feed materials include: wheat, barley, rye, oats, by products from cereals, such as corn gluten meal, Distillers Dried Grain Solubles (DDGS), wheat bran, wheat middlings, wheat shorts, rice bran, rice hulls, oat hulls, palm kernel, and citrus pulp. Some protein sources may also be regarded as high fibre: protein obtained from sources such as sunflower, lupin, fava beans and cotton.

As described herein, feed may be one or more of the following: a compound feed and premix, including pellets, nuts or (cattle) cake; a crop or crop residue: corn, soybeans, sorghum, oats, barley, corn stover, copra, straw, chaff, sugar beet waste; fish meal; freshly cut grass and other forage plants; meat and bone meal; molasses; oil cake and press cake; oligosaccharides; conserved forage plants: hay and silage; seaweed; seeds and grains, either whole or prepared by crushing, milling etc.; sprouted grains and legumes; yeast extract.

The term feed as used herein also encompasses in some embodiments pet food. A pet food is plant or animal material intended for consumption by pets, such as dog food or cat food. Pet food, such as dog and cat food, may be either in a dry form, such as kibble for dogs, or wet canned form. Cat food may contain the amino acid taurine.

The term feed may also encompass in some embodiments fish food. A fish food normally contains macro nutrients, trace elements and vitamins necessary to keep captive fish in good health. Fish food may be in the form of a flake, pellet or tablet. Pelleted forms, some of which sink rapidly, are often used for larger fish or bottom feeding species. Some fish foods also contain additives, such as beta carotene or sex hormones, to artificially enhance the color of ornamental fish.

Also encompassed within the term "feed" is bird food including food that is used both in birdfeeders and to feed pet birds. Typically, bird food comprises of a variety of seeds, but may also encompass suet (beef or mutton fat).

As used herein the term "contacted" refers to the indirect or direct application of the feed additive composition to the product (e.g. the feed). Examples of the application methods which may be used, include, but are not limited to, treating the product in a material comprising the feed additive composition, direct application by mixing the feed additive composition with the product, spraying the feed additive composition onto the product surface or dipping the product into a preparation of the feed additive composition.

The Bacillus-based component may be preferably admixed with the product (e.g. feedstuff). Alternatively, it may be included in the emulsion or raw ingredients of a feedstuff.

For some applications, it is important that it is made available on or to the surface of a product to be affected/treated.

The Bacillus-based component may be applied to intersperse, coat and/or impregnate a product (e.g. feedstuff or raw ingredients of a feedstuff) with a controlled amount of a Bacillus-based component.

The DFM comprising at least one bacterial strain can be added in suitable concentrations, for example, in concentrations in the final feed product which offer a daily dose of between about $2\times10^3$ CFU/g of feed to about $2\times10^{11}$ CFU/g of feed, suitably between about $2\times10^6$ to about $1\times10^{10}$, suitably between about $3.75\times10^7$ CFU/g of feed to about $1\times10^{10}$ CFU/g of feed.

Preferably, the Bacillus-based component will be thermally stable to heat treatment up to about 70° C.; up to about 85° C.; or up to about 95° C. The heat treatment may be performed from about 30 seconds up to several minutes. The term "thermally stable" means that at least about 50% of Bacillus-based component that was present/active before heating to the specified temperature are still present/active after it cools to room temperature. In a particularly preferred embodiment the Bacillus-based component is homogenized to produce a powder.

Alternatively, the Bacillus-based component is formulated to granules as described in WO2007/044968 (referred to as TPT granules) incorporated herein by reference.

In another preferred embodiment when the feed additive composition is formulated into granules, the granules comprise a hydrated barrier salt coated over the protein core. The advantage of such salt coating is improved thermo-tolerance, improved storage stability and protection against other feed additives otherwise having adverse effect on the at least one protease and/or DFM comprising one or more bacterial strains. Preferably, the salt used for the salt coating has a water activity greater than 0.25 or constant humidity greater than 60% at 20° C. Preferably, the salt coating comprises a $Na_2SO_4$.

Feed containing the Bacillus-based component may be produced using a feed pelleting process. Optionally, the pelleting step may include a steam treatment, or conditioning stage, prior to formation of the pellets. The mixture comprising the powder may be placed in a conditioner, e.g. a mixer with steam injection. The mixture is heated in the conditioner up to a specified temperature, such as from 60-100° C., typical temperatures would be 70° C., 80° C., 85° C., 90° C. or 95° C. The residence time can be variable from seconds to minutes and even hours. Such as 5 seconds, 10 seconds, 15 seconds, 30 seconds, 1 minutes 2 minutes, 5 minutes, 10 minutes, 15 minutes, 30 minutes and 1 hour.

With regard to the granule at least one coating may comprise a moisture hydrating material that constitutes at least 55% w/w of the granule; and/or at least one coating may comprise two coatings. The two coatings may be a moisture hydrating coating and a moisture barrier coating. In some embodiments, the moisture hydrating coating may be between 25% and 60% w/w of the granule and the moisture barrier coating may be between 2% and 15% w/w of the granule. The moisture hydrating coating may be selected from inorganic salts, sucrose, starch, and maltodextrin and the moisture barrier coating may be selected from polymers, gums, whey and starch.

The granule may be produced using a feed pelleting process and the feed pretreatment process may be conducted between 70° C. and 95° C. for up to several minutes, such as between 85° C. and 95° C.

The Bacillus-based component may be formulated to a granule for animal feed comprising: a core; an active agent, the active agent of the granule retaining at least 80% activity after storage and after a steam-heated pelleting process where the granule is an ingredient; a moisture barrier coating; and a moisture hydrating coating that is at least 25% w/w of the granule, the granule having a water activity of less than 0.5 prior to the steam-heated pelleting process.

The granule may have a moisture barrier coating selected from polymers and gums and the moisture hydrating material may be an inorganic salt. The moisture hydrating coating may be between 25% and 45% w/w of the granule and the moisture barrier coating may be between 2% and 10% w/w of the granule.

A granule may be produced using a steam-heated pelleting process which may be conducted between 85° C. and 95° C. for up to several minutes.

Alternatively, the composition is in a liquid formulation suitable for consumption preferably such liquid consumption contains one or more of the following: a buffer, salt, sorbitol and/or glycerol.

Also, the feed additive composition may be formulated by applying, e.g. spraying, the *Bacillus*-based component onto a carrier substrate, such as ground wheat for example.

In one embodiment, such feed additive composition comprising a *Bacillus*-based component as described herein may be formulated as a premix. By way of example only the premix may comprise one or more feed components, such as one or more minerals and/or one or more vitamins.

Alternatively, the composition is in a liquid formulation suitable for consumption preferably such liquid consumption contains one or more of the following: a buffer, salt, sorbitol and/or glycerol.

Also, the feed additive composition may be formulated by applying, e.g., spraying, the *Bacillus*-based component onto a carrier substrate, such as ground wheat for example.

In one embodiment such *Bacillus*-based component as described herein may be formulated as a premix. By way of example only the premix may comprise one or more feed components, such as one or more minerals and/or one or more vitamins.

It will be understood that *Bacillus*-based component as disclosed herein is suitable for addition to any appropriate feed material.

As used herein, the term feed material refers to the basic feed material to be consumed by an animal. It will be further understood that this may comprise, for example, at least one or more unprocessed grains, and/or processed plant and/or animal material such as soybean meal or bone meal.

It will be understood by the skilled person that different animals require different feedstuffs, and even the same animal may require different feedstuffs, depending upon the purpose for which the animal is reared.

Preferably, the feedstuff may comprise feed materials comprising maize or corn, wheat, barley, triticale, rye, rice, tapioca, sorghum, and/or any of the by-products, as well as protein rich components like soybean mean, rape seed meal, canola meal, cotton seed meal, sunflower seed mean, animal-by-product meals and mixtures thereof. More preferably, the feedstuff may comprise animal fats and/or vegetable oils.

Optionally, the feedstuff may also contain additional minerals such as, for example, calcium and/or additional vitamins. Preferably, the feedstuff is a corn soybean meal mix.

In another aspect, there is provided a method for producing a feedstuff. Feedstuff is typically produced in feed mills in which raw materials are first ground to a suitable particle size and then mixed with appropriate additives. The feedstuff may then be produced as a mash or pellets; the later typically involves a method by which the temperature is raised to a target level and then the feed is passed through a die to produce pellets of a particular size. The pellets are allowed to cool. Subsequently liquid additives such as fat and enzyme may be added. Production of feedstuff may also involve an additional step that includes extrusion or expansion prior to pelleting, in particular, by suitable techniques that may include at least the use of steam.

The feedstuff may be a feedstuff for a monogastric animal, such as poultry (for example, broiler, layer, broiler breeders, turkey, duck, geese, water fowl), swine (all age categories), a pet (for example dogs, cats) or fish, preferably the feedstuff is for poultry.

The *Bacillus*-based component described herein may be placed on top of the animal feed, i.e., top fed. Alternatively, the *Bacillus*-based component described herein may be added to a liquid such as in the drinking water of the animal.

As used herein the term "contacted" refers to the indirect or direct application of a *Bacillus*-based component as described herein to a product (e.g. the feed).

Examples of application methods which may be used, include, but are not limited to, treating the product in a material comprising the *Bacillus*-based component, direct application by mixing a feed additive composition *Bacillus*-based component as described herein with the product, spraying such feed additive composition onto the product surface or dipping the product into a preparation of the feed additive composition. In one embodiment a feed additive composition *Bacillus*-based component as described herein is preferably admixed with the product (e.g. feedstuff). Alternatively, the feed additive composition may be included in the emulsion or raw ingredients of a feedstuff. This allows the composition to impart a performance benefit.

A method of preparing the *Bacillus*-based component as described herein may also comprise the further step of pelleting the powder. The powder may be mixed with other components known in the art. The powder, or mixture comprising the powder, may be forced through a die and the resulting strands are cut into suitable pellets of variable length.

Optionally, the pelleting step may include a steam treatment, or conditioning stage, prior to formation of the pellets. The mixture comprising the powder may be placed in a conditioner, e.g. a mixer with steam injection. The mixture is heated in the conditioner up to a specified temperature, such as from 60-100° C., typical temperatures would be 70° C., 80° C., 85° C., 90° C. or 95° C. The residence time can be variable from seconds to minutes and even hours. Such as 5 seconds, 10 seconds, 15 seconds, 30 seconds, 1 minute, 2 minutes, 5 minutes, 10 minutes, 15 minutes, 30 minutes and 1 hour.

It will be understood by the skilled person that different animals require different feedstuffs, and even the same animal may require different feedstuffs, depending upon the purpose for which the animal is reared.

Optionally, the feedstuff may also contain additional minerals such as, for example, calcium and/or additional vitamins. In some embodiments, the feedstuff is a corn soybean meal mix.

Feedstuff is typically produced in feed mills in which raw materials are first ground to a suitable particle size and then mixed with appropriate additives. The feedstuff may then be produced as a mash or pellets; the later typically involves a method by which the temperature is raised to a target level and then the feed is passed through a die to produce pellets of a particular size. The pellets are allowed to cool. Subsequently liquid additives such as fat and enzyme may be added. Production of feedstuff may also involve an additional step that includes extrusion or expansion prior to pelleting, in particular by suitable techniques that may include at least the use of steam.

As was noted above, the *Bacillus*-based component and/or a feedstuff comprising the same may be used in any suitable form. It may be used in the form of solid or liquid preparations or alternatives thereof. Examples of solid preparations include powders, pastes, boluses, capsules, pellets, tablets, dusts, and granules which may be wettable, spray-dried or freeze-dried. Examples of liquid preparations include, but are not limited to, aqueous, organic or aqueous-organic solutions, suspensions and emulsions.

In some applications, the feed additive compositions may be mixed with feed or administered in the drinking water.

A *Bacillus*-based component, comprising admixing a *Bacillus*-based component as described herein with a feed acceptable carrier, diluent or excipient, and (optionally) packaging.

The feedstuff and/or *Bacillus*-based component may be combined with at least one mineral and/or at least one vitamin. The compositions thus derived may be referred to herein as a premix. The feedstuff may comprise at least 0.0001% by weight of *Bacillus*-based component. Suitably, the feedstuff may comprise at least 0.0005%; at least 0.0010%; at least 0.0020%; at least 0.0025%; at least 0.0050%; at least 0.0100%; at least 0.020%; at least 0.100% at least 0.200%; at least 0.250%; at least 0.500% by weight of the *Bacillus*-based component.

Preferably, a food or *Bacillus*-based component may further comprise at least one physiologically acceptable carrier. The physiologically acceptable carrier is preferably selected from at least one of maltodextrin, limestone (calcium carbonate), cyclodextrin, wheat or a wheat component, sucrose, starch, Na[2]S0[4], Talc, PVA and mixtures thereof. In a further embodiment, the food or feed may further comprise a metal ion chelator. The metal ion chelator may be selected from EDTA or citric acid.

In one embodiment a *Bacillus*-based component as described herein (whether or not encapsulated) can be formulated with at least one physiologically acceptable carrier selected from at least one of maltodextrin, limestone (calcium carbonate), cyclodextrin, wheat or a wheat component, sucrose, starch, $Na_2SO_4$, Talc, PVA, sorbitol, benzoate, sorbate, glycerol, sucrose, propylene glycol, 1,3-propane diol, glucose, parabens, sodium chloride, citrate, acetate, phosphate, calcium, metabisulfite, formate and mixtures thereof.

In some embodiments, a *Bacillus*-based component as described herein, will be in a physiologically acceptable carrier. Suitable carriers may be large, slowly metabolized macromolecules such as proteins, polypeptides, liposomes, polysaccharides, polylactic acids, polyglycolic acids, polymeric amino acids, amino acid copolymers and inactive virus particles. Pharmaceutically acceptable salts can be used, for example mineral acid salts, such as hydrochlorides, hydrobromides, phosphates and sulphates, or salts of organic acids, such as acetates, propionates, malonates and benzoates. Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, capsules, liquids, gels, syrups, slurries and suspensions, for ingestion by the patient. Once formulated, the can be administered directly to the subject. The subjects to be treated can be animals.

Non-limiting examples of compositions and methods disclosed herein include:

1. A method for inhibiting or delaying all or part of the growth of pathogenic *Enteroccocus* spp. in an animal which comprises administering an effective amount of at least one *Bacillus*-based component selected from the group consisting of: a *Bacillus*-based direct fed microbial comprising one or more *Bacillus* bacterial strains, a supernatant obtained from a *Bacillus* culture or a combination thereof to an animal.

2. The method of embodiment 1 wherein the *Bacillus*-based direct fed microbial is selected from the group consisting of *Bacillus amyloliquefaciens*, *Bacillus licheniformis*, *Bacillus pumilis* and *Bacillus subtilis*.

3. The method of embodiment 1 or 2 wherein the *Bacillus*-based direct fed microbial is selected one or more of the following strains: *Bacillus* strain 2084 Accession No. NRR1 B-50013, *Bacillus* strain LSSAO1 Accession No. NRRL B-50104 and *Bacillus* strain 15A-P4 ATCC Accession No. PTA-6507.

4. The method of embodiment 1, 2 or 3wherein the animal is a monogastric animal.

5. The method of embodiment, 1, 2 or 3wherein the animal is a multigastric animal.

6. The method of embodiment of 1, 2 3 or 4wherein the monogastric animal is poultry.

7. The method of any of embodiments 1-6 above, wherein the at least one *Bacillus*-based component is administered directly to an animal through animal feed whether in the feed or on top of the feed or in a liquid such as water.

8. The method of any embodiment 1-7, wherein the at least one *Bacillus*-based component is administered to the animal in a form selected from the group consisting of a feedstuff, a feed additive composition, a premix or in a liquid such as water.

EXAMPLE

Unless defined otherwise herein, all technical and scientific terms used herein have the same meaning as commonly understood by one of ordinary skill in the art to which this disclosure belongs. Singleton, et al., *DICTIONARY OF MICROBIOLOGY AND MOLECULAR BIOLOGY*, 2D ED., John Wiley and Sons, New York (1994), and Hale & Marham, *THE HARPER COLLINS DICTIONARY OF BIOLOGY*, Harper Perennial, N.Y. (1991) provide one of skill with a general dictionary of many of the terms used with this disclosure.

The disclosure is further defined in the following Examples. It should be understood that the Examples, while indicating certain embodiments, is given by way of illustration only. From the above discussion and the Examples, one skilled in the art can ascertain essential characteristics of this disclosure, and without departing from the spirit and scope thereof, can make various changes and modifications to adapt to various uses and conditions.

Example 1

*Enterococcus cecorum* and *Bacillus* Strains

Fifty-two *Enterococcus cecorum* strains were collected from culture collections in North America and Europe, as summarized in Table 1 below. During collection, emphasis was placed on sourcing *Enterococcus cecorum* strains isolated from extra-intestinal lesions and confirmed spondylitis outbreaks, allowing confidence that the tested strains were virulent and capable of causing disease.

TABLE 1

*Enterococcus cecorum* strains used in this study

| Internal Strain Designation | Geographic Origin | Biological Origin | Year of Isolation | Source |
|---|---|---|---|---|
| 11915-3 | North Carolina, USA | Spinal abscess | 2013 | DuPont Internal Collection |
| 11937-2 | North Carolina, USA | Spinal abscess | 2013 | DuPont Internal Collection |
| 11944-2 | North Carolina, USA | Spinal abscess | 2013 | DuPont Internal Collection |
| 12108-2 | Delaware, USA | Spinal abscess | 2013 | DuPont Internal Collection |
| 11976-5 | North Carolina, USA | Caecal Swab | 2013 | DuPont Internal Collection |
| 12123-1 | Delaware, USA | GIT | 2013 | DuPont Internal Collection |
| 12476-5 | Delaware, USA | Spinal abscess | 2013 | DuPont Internal Collection |
| 11914-3 | North Carolina, USA | Spinal abscess | 2013 | DuPont Internal Collection |
| 12147-1 ** | North Carolina, USA | Spinal abscess | 2013 | DuPont Internal Collection |
| 14191-2 | Minnesota, USA | Spinal abscess | 2014 | DuPont Internal Collection |
| 14201-1 | Minnesota, USA | Spinal abscess | 2014 | DuPont Internal Collection |
| 11920-1 | North Carolina, USA | Spinal abscess | 2013 | DuPont Internal Collection |
| 12161-6 | North Carolina, USA | GIT | 2013 | DuPont Internal Collection |
| 14194-5 | Minnesota, USA | Spinal abscess | 2014 | DuPont Internal Collection |
| 11955-1 | North Carolina, USA | Spinal abscess | 2013 | DuPont Internal Collection |
| 14192-2 | Minnesota, USA | Spinal abscess | 2014 | DuPont Internal Collection |
| 11976-2 | North Carolina, USA | Cecal Swab | 2013 | DuPont Internal Collection |
| 11952-1 | North Carolina, USA | Spinal abscess | 2013 | DuPont Internal Collection |
| 12163-2 | North Carolina, USA | GIT | 2013 | DuPont Internal Collection |
| 14202-4 | Minnesota, USA | Spinal abscess | 2014 | DuPont Internal Collection |
| 11960-1 | North Carolina, USA | Spinal abscess | 2013 | DuPont Internal Collection |
| 12696M-1 ** | North Carolina, USA | Spinal Abscess | 2013 | DuPont Internal Collection |
| 12418-1 | Minnesota, USA | GIT | 2013 | DuPont Internal Collection |
| 11957-3 ** | North Carolina, USA | Spinal abscess | 2013 | DuPont Internal Collection |
| 12435-3 | Minnesota, USA | Ceca | 2013 | DuPont Internal Collection |
| 11951-1 ** | North Carolina, USA | Spinal abscess | 2013 | DuPont Internal Collection |
| 12119-2 | Delaware, USA | GIT | 2013 | DuPont Internal Collection |
| 904971 | Pennsylvania, USA | yolk sac 2 | | Penn State University |
| 903797 | Pennsylvania, USA | chicken knee | | Penn State University |
| 900118 | Pennsylvania, USA | Liver | | Penn State University |
| 843323 | Pennsylvania, USA | chicken bone | | Penn State University |
| 842805 | Pennsylvania, USA | chicken pericardium | | Penn State University |
| 841976 | Pennsylvania, USA | chicken bone dead 1 | | Penn State University |
| 840394 | Pennsylvania, USA | chicken bone 2 | | Penn State University |
| 840387 | Pennsylvania, USA | chicken knee | | Penn State University |
| 910525 | Pennsylvania, USA | Spinal abscess | | Penn State University |
| 209247 | Pennsylvania, USA | Bone Marrow | | Penn State University |
| E.58.33 | Belgium | femoral head | 2014 | PoulPharm |
| E.53.14 | Belgium | femur | 2014 | PoulPharm |
| E.59.56 ** | Belgium | femoral head | 2014 | PoulPharm |
| F.68.19 ** | Belgium | joint | 2015 | PoulPharm |
| C.34.19 ** | Belgium | Bone Marrow | 2013 | PoulPharm |
| D.42.11 | Belgium | joint | 2013 | PoulPharm |
| D.44.11 ** | Belgium | Bone Marrow | 2014 | PoulPharm |
| D.45.08 | Belgium | joint | 2014 | PoulPharm |
| G.84.68 | Belgium | Bone Marrow | 2015 | PoulPharm |
| J.5.76 | Belgium | hock joint | 2015 | PoulPharm |
| G.77.23 | Belgium | femur marrow | 2015 | PoulPharm |
| G.75.17 ** | Belgium | articulation | 2015 | PoulPharm |
| G.80.72 | Belgium | femoral head | 2015 | PoulPharm |
| G.79.39 | Belgium | bone marrow | 2015 | PoulPharm |
| J.6.81 | Belgium | femur marrow | 2015 | PoulPharm |

** - strain used in non-DuPont strain testing

The inhibitory potential of 11 *Bacillus* strains was tested in total. These included both DuPont proprietary DFM strains and *Bacillus* isolated from competitor DFM products, as summarized in Table 2. All tested *Bacillus* strains are commercialized for use in poultry production. Enviva® PRO which is commercially available from Danisco A/S is a combination of *Bacillus* strain 2084 Accession No. NRR1 B-50013, *Bacillus* strain LSSAO1 Accession No. NRRL B-50104 and *Bacillus* strain 15A-P4 ATCC Accession No. PTA-6507 (as taught in U.S. Pat. No. 7,754,469 B—incorporated herein by reference).

TABLE 2

DFM *Bacillus* strains tested in this study

| Internal Strain Designation | Strain Commercial Designation | Species (label claim) | Commercial Product Name | Producing Company |
|---|---|---|---|---|
| BS8 | NRRL B-50104 | *Bacillus amyloliquefaciens* | Enviva ® PRO | DuPont |

TABLE 2-continued

DFM Bacillus strains tested in this study

| Internal Strain Designation | Strain Commercial Designation | Species (label claim) | Commercial Product Name | Producing Company |
|---|---|---|---|---|
| 2084 | NRRL B-50013 | Bacillus amyloliquefaciens | Enviva ® PRO | DuPont |
| 15A-P4 | PTA-6507 | Bacillus amyloliquefaciens | Enviva ® PRO | DuPont |
| CS1 | C-3102 DSM15544 | Bacillus subtilis | Calsporin | Calpis |
| 2B1 | DSM5750 | Bacillus subtilis | BioPlus 2B | Chr Hansen |
| 2B2 | DSM5749 | Bacillus licheniformis | BioPlus 2B | Chr Hansen |
| #11/1 | DSM17299 | Bacillus subtilis | Gallipro | Chr Hansen |
| #12/1 | DSM17236 | Bacillus licheniformis | Gallipro Tect | Chr Hansen |
| #10/4 | | Bacillus subtilis | Sporulin | Novus |
| #10B/1 | | Bacillus subtilis | Sporulin | Novus |
| #10B/4 | | Bacillus subtilis | Sporulin | Novus |

All non-DuPont *Bacillus* products were purchased, and isolated in triplicate from 3 separate production batches. All strains were identified in order to ensure that the strains recovered matched the strain claims on the product label. Non-DuPont products were tested against a subset of 9 isolates from the full *Enterococcus cecorum* collection, as denoted in Table 2 above.

Example 2

Production of Cell Free Supernantants (CFS) and Growth of *Enterococcus cecorum*, *Enterococcus avium* and *Enterococcus gallinarum* Strains An inoculating loop is used to inoculate a 30 ml shaker tube with 10 ml tryptic soy broth (TSB) from a frozen *Bacillus* stock. The tube is incubated in a 32° C. incubator for 24 hours and shaken at 130 to grow the *Bacillus*.

The optical density (OD) was checked on a spectrometer (wavelength 600 nm, absorbance 0) after incubating flasks for 18 hours. 2 ml of sterile TSB was pipetted into a cuvette to create a blank control. A 10× dilution of *Bacillus* was created by pipetting 1.8 ml sterile TSB and 0.2 ml of 18 hr growth into each cuvette. Cuvettes were covered and inverted to ensure thorough mixing. The absorbance of the *Bacillus* dilutions was determined to be between 0.25 and 0.3 (samples with absorbance readings below 0.25 were re-incubated until absorbance reached acceptable levels).

The *Bacillus* growth was transferred from each flask into sterile 250 ml centrifuge bottles and centrifuged at 10,000 rpm for 10 minutes. After centrifuging, the supernatants of each *Bacillus* type were transferred to a Nalgene bottle top filter and pumped into 50 ml conical tubes.

This procedure was followed for all *Bacillus* strains. Cell Free Supernatant (CFS) was then frozen at −80° C. until required.

*E. cecorum* strains were inoculated from deep frozen stock cultures in a BHI (brain and heart infusion) broth and a BHI agar plate (to check purity) and incubated overnight at 37° C. All strains were subcultured at least twice before inclusion in the assay to ensure adaptation to the growth medium.

All assays were performed in duplicate for each *Bacillus*-based DFM identified in Table 2 above.

20 ml of BHI broth was incubated for 1 hour prior to assaying, to avoid thermic shock for the *Enterococcus cecorum* cells.

In a 96-well UV treated microtiter plate with flat-bottom wells, the medium (BHI broth) and the CFS and target microorganism were added as follows:

Positive control: 200 µl medium+2 µl bacterium (1%)
Negative control: 200 µl medium
CFS assay well: 180 µl medium+20 µl CFS+2 µl bacterium (1%)
Negative CFS well: 180 µl medium+20 µl CFS Plates were incubated for 14 hours at 37° C. in a Flex station machine to record absorbance, with data transferred directly to a computer for analysis. Measurements were taken every 15 minutes.

Results are given as % of inhibition comparing control at OD=0.4 (*E. cecorum* alone) and treated (*E. cecorum* incubated with *Bacillus* CFS). Over 42 individual strains, average inhibition by each of the 3 Enviva® PRO strains (*Bacillus*-based component) was >85%, as shown in FIG. 1. It was determined that >50% inhibition is considered acceptable and >75% inhibition is considered excellent. Inhibition over 100% indicates that the pathogen isolate has been lysed by the *Bacillus*, rather than simply inhibited.

Table 3 shows the average growth inhibition of 51 *Enterococcus cecorum* strains by Enviva® PRO strains. All strains were capable of significantly inhibiting the growth of *Enterococcus cecorum*, compared to *E. cecorum* incubated without *Bacillus* CFS. The most effective strain was 15AP4 (*Bacillus*-based component), with an average inhibition of 88.79%, though differences between strains were not statistically significant.

TABLE 3

Average inhibition of *Enterococcus cecorum* strains collected from American and European poultry production by 3 *Bacillus* DFM strains (*Bacillus*-based component)

| | European strains | | American strains | | All strains | |
|---|---|---|---|---|---|---|
| | Average Inhibition, % | SEM | Average Inhibition, % | SEM | Average Inhibition, % | SEM |
| 15AP4 | 88.27 | 2.887 | 89.03 | 3.086 | 88.79 | 2.30 |
| BS2084 | 89.87 | 2.887 | 88.08 | 2.955 | 88.60 | 2.233 |
| BS8 | 86.80 | 2.887 | 84.24 | 2.955 | 84.99 | 2.233 |
| P-value | 0.7552 | | 0.4898 | | 0.4054 | |

Table 4 shows the average growth inhibition of a subset of 9 *Enterococcus cecorum* strains by 12 *Bacillus* strains. The most effective strain was BS2084 (*Bacillus*-based component), with an average inhibition of 85.33%. The least effective *Bacillus* strain was 2B2, with an average inhibition of −80.17%, indicating that the *Enterococcus cecorum* grew faster in the presence of the *Bacillus* CFS (*Bacillus*-based component), then in its absence. There were significant differences in efficacy among *Bacillus* strains.

Figure 6:
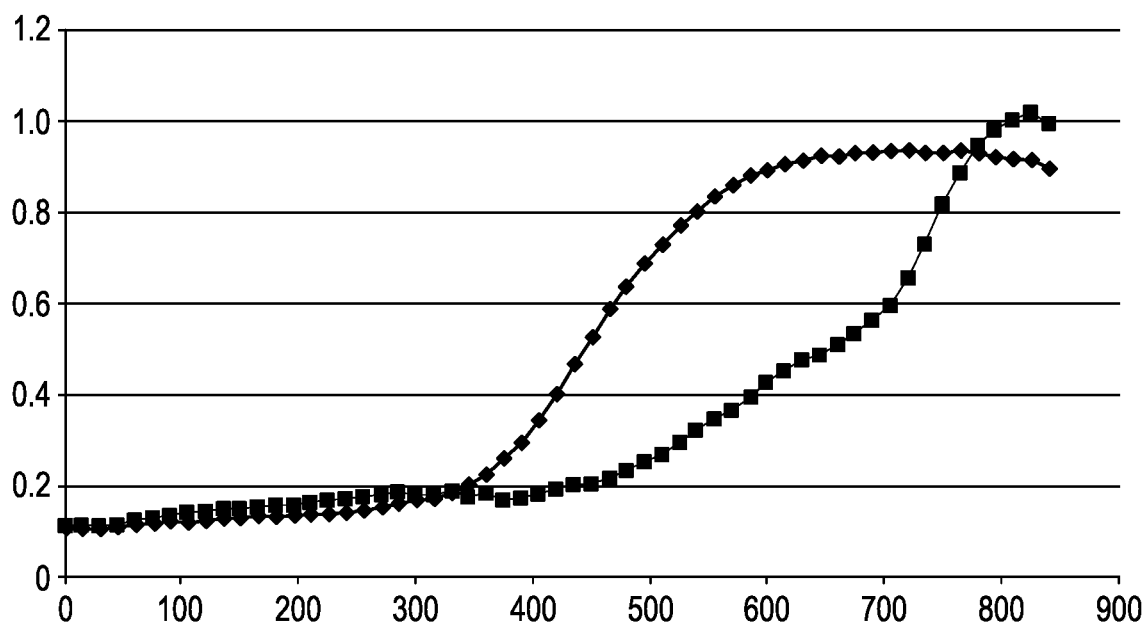
FIG. 6 shows growth profiles of Enterococcus avium E 84197 incubated or not with CFS of Bacillus 2084.

FIG. 6 shows growth profiles of *Enterococcus avium* E 84197 incubated or not with CFS of *Bacillus* 2084 (*Bacillus*-based component).

TABLE 4

Average growth inhibition of 11 *Enterococcus cecorum* strains by 11 *Bacillus* DFM strains

|  | 15AP4 | BS2084 | BS8 | CS1 | #11/1 | #12/1 | #10/4 | #10B/1 | #10B/4 | 2B1 | 2B2 |
|---|---|---|---|---|---|---|---|---|---|---|---|
| 11951-1 | 73.90 | 89.09 | 73.49 | −23.50 | 47.98 | 31.67 | 36.26 | — | — | 37.57 | 31.80 |
| 11957-3 | 102.15 | 102.39 | 99.83 | 97.67 | −6.57 | 25.89 | −11.83 | 52.68 | −6.57 | −55.86 | −2.80 |
| 11960-1 | 93.12 | 88.99 | 74.47 | 83.30 | −54.90 | −5.51 | 32.99 | 94.25 | 51.11 | −83.02 | −50.94 |
| 12696M-1 | 32.17 | 49.62 | 67.50 | 99.12 | −0.10 | 15.12 | −15.19 | 100.36 | 73.90 | −17.63 | −6.77 |
| C.34.19 | 89.79 | 77.34 | 75.19 | 99.35 | −6.28 | 5.25 | −25.09 | 94.81 | 53.57 | −67.24 | −40.41 |
| D.42.11 | 98.69 | 99.40 | 99.30 | 86.33 | −67.20 | −35.45 | −29.53 | 50.36 | 25.55 | −128.06 | −54.36 |
| E.59.56 | 50.60 | 84.74 | 71.20 | 86.33 | −16.02 | −6.04 | −8.02 | 82.07 | 57.95 | −146.62 | −87.93 |
| F.68.19 | 89.38 | 83.21 | 78.16 | 79.76 | −4.68 | −9.61 | −13.67 | 66.94 | 23.08 | −121.79 | −41.97 |
| G.75.17 | 100.99 | 93.22 | 97.43 | 79.76 | −81.97 | −9.07 | −77.68 | 69.90 | 32.96 | −138.92 | −35.45 |
| Average[1] | 81.20$^a$ | 85.33$^a$ | 81.84$^a$ | 76.46$^a$ | −21.04$^c$ | 1.36$^{bc}$ | 42.41$^{bc}$ | 76.46$^a$ | 38.94$^{ab}$ | −80.17$^d$ | −32.09$^{cd}$ |
| Std Err | 8.176 | 5.168 | 4.365 | 12.771 | 13.391 | 6.883 | 11.287 | 6.861 | 8.948 | 20.559 | 11.624 |

[1]P-value = P <0.0001; $^{a,b,c}$Values within a row without common superscripts are significantly different at P <0.05

REFERENCE

Verslyppe B, De Smet W, De Baets B, De Vos P, Dawyndt P 2014. StrainInfo introduces electronic passports for microorganisms. Syst Appl Microbiol. 37(1):42-50.

The data in Table 5 demonstrates the antimicrobial activity of the CFSs of *B. amyloliquefaciens* subsp. *plantarum* 15AP4, BS8 and 2084 (*Bacillus*-based component), against *Enterococcus gallinarum* VTT E-97776T.

FIG. 7 shows the antimicrobial activity of the CFSs of *Bacillus amyloliquefaciens* DSM7$^T$, *B. subtilis* DSM10$^T$ and *B. licheniformis* DSM13$^T$ against 10 clinical isolates *Enterococcus cecorum* isolated from poultry production system in the US and in Belgium, expressed as % of inhibition at the exact end-point when the control pathogen curve reaches OD 0.4 (black bars correspond to the average % of inhibition).

TABLE 5

In vitro delay of growth of a culture of *Enterococcus gallinarum* VTT E-97776T induced by *Bacillus*-based component-CFSs of *Bacillus amyloliquefaciens* subsp. plantarum 15AP4, BS8 and 2084.

| | *Enterococcus gallinarum* VTT E-97776T | | | | | | | | |
|---|---|---|---|---|---|---|---|---|---|
| | control | | | | treatment | | | | Growth |
| | ODcatT0 | ODc0,4 (nearest) | Tc(time at OD0,4) | | ODtatT0 | 0DatTc | Tt(time at OD0,4) | 0Dt0,4(nearest) | delay |
| 15AP4 | 0.10965 | 0.42265 | 06:45:00 | 405 | 0.11045 | 0.18645 | 08:15:00 | 495 | 0.3965 | 01:30:00 |
| BS8 | 0.11355 | 0.4004 | 06:15:00 | 405 | 0.11055 | 0.15675 | 10:00:00 | 600 | 0.4215 | 03:15:00 |
| 2084 | 0.10985 | 0.40595 | 06:15:00 | 375 | 0.10735 | 0.1471 | 09:30:00 | 570 | 0.3838 | 03:15:00 |

Figure 2:
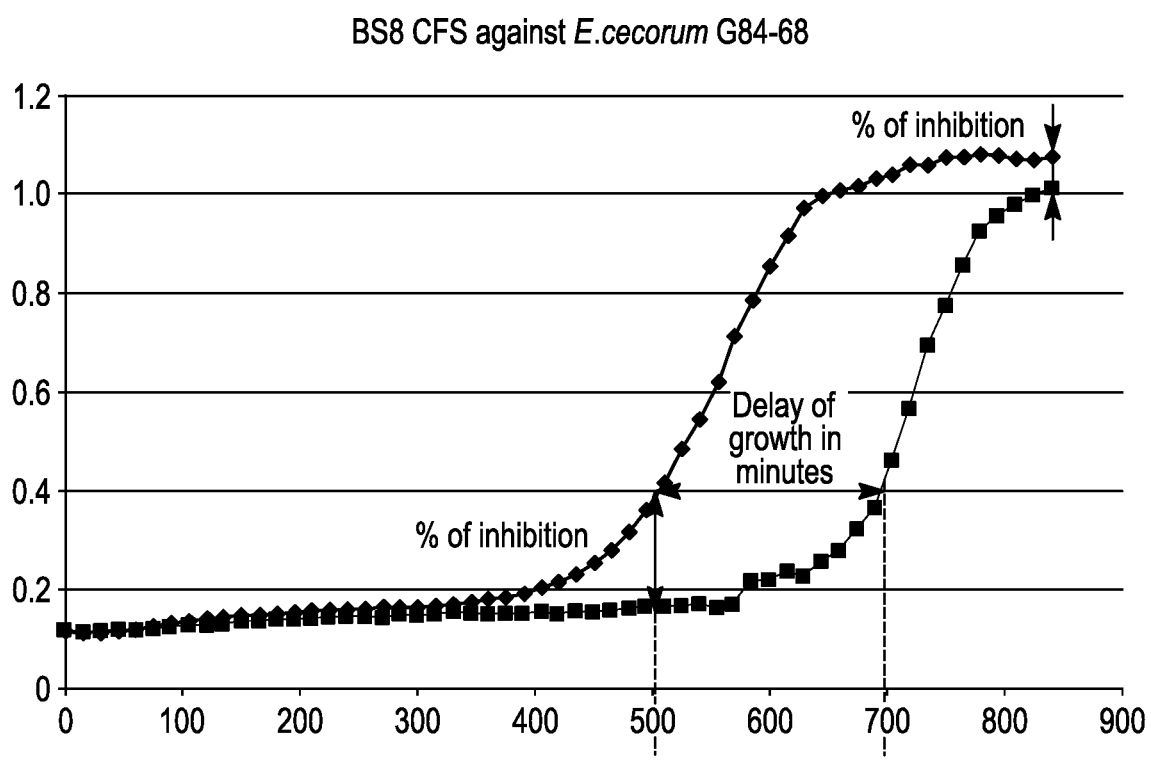
FIG. 2 depicts data on the kinetics of E. cecorum strain G84-68 growth with/without Bacillus BS8.

FIGS. 1 and 2 show the average inhibition for the *E. cecorum* strains collected from American and European poultry production, respectively.

Figure 3:
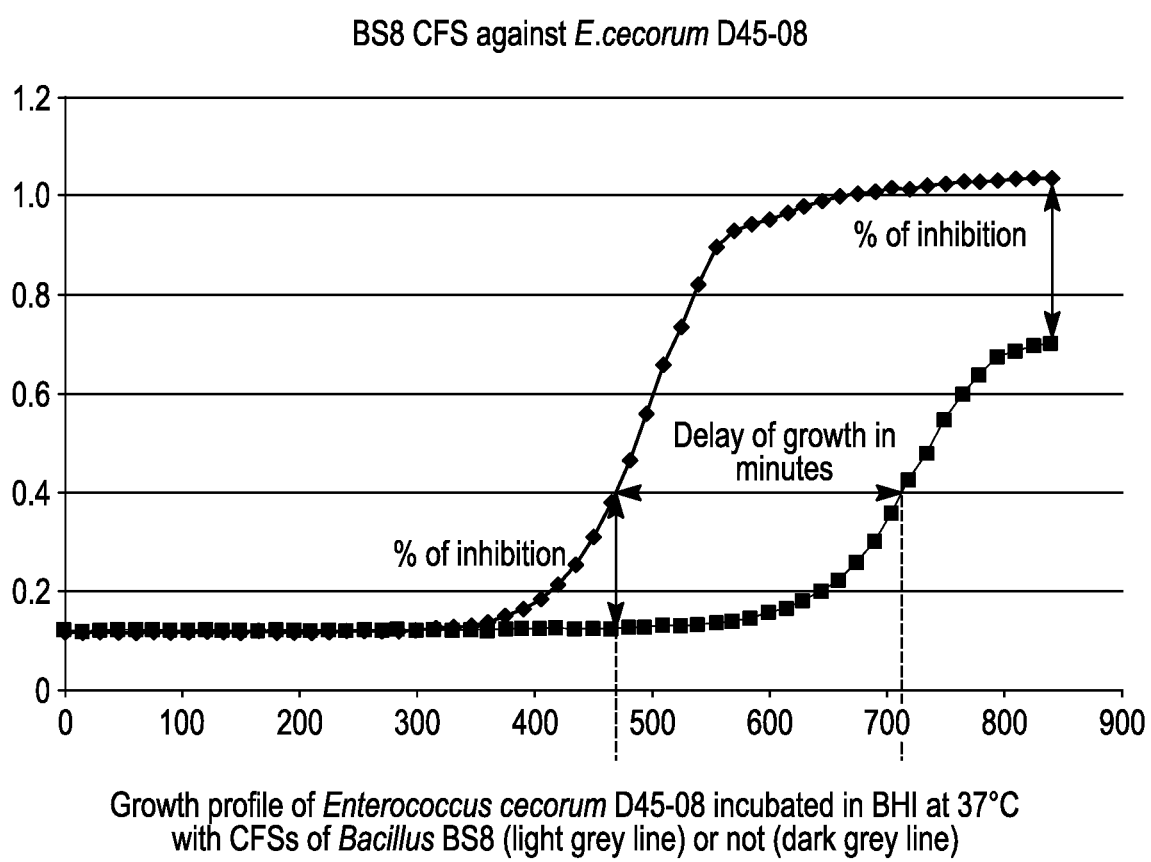
FIG. 3 depicts data on the kinetics of E. cecorum strain D45-08 growth with/without Bacillus BS8.
Figure 4:
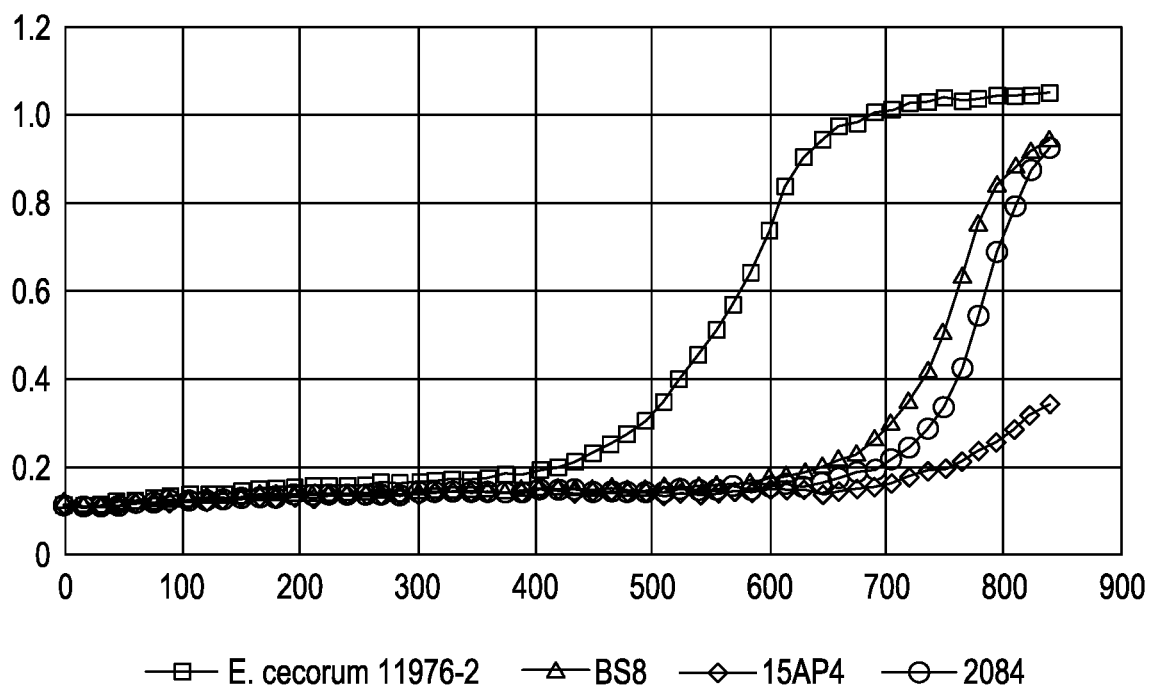
FIG. 4 depicts the growth inhibition profile of Enterococcus cecorum strain 11976-2 incubated with or without a cell free supernatant (CFS) of Bacillus BS8, Bacillus 15AP4 or Bacillus 2084.

FIG. 3 depicts data on the kinetics of *E. cecorum* growth with/without the Enviva® PRO strains. Some *E. cecorum* are not fully inhibited by the *Bacillus* supernatants, i.e., a *Bacillus*-based component. At the end of the 14 h incubation time, the concentrations of the pathogen are the same for control and treated plates, but the lag phase is extended and exponential growth delayed. Given the gut transit time of poultry, this kind of result would mean that (despite the lack of overall inhibition) that the *Bacillus*-based component could prevent proliferation of the pathogen during its passage through the gut, reducing the risk of adhesion and translocation. Other strains are both delayed and inhibited at the 14 h time point, as demonstrated in FIG. 4.

Figure 5:
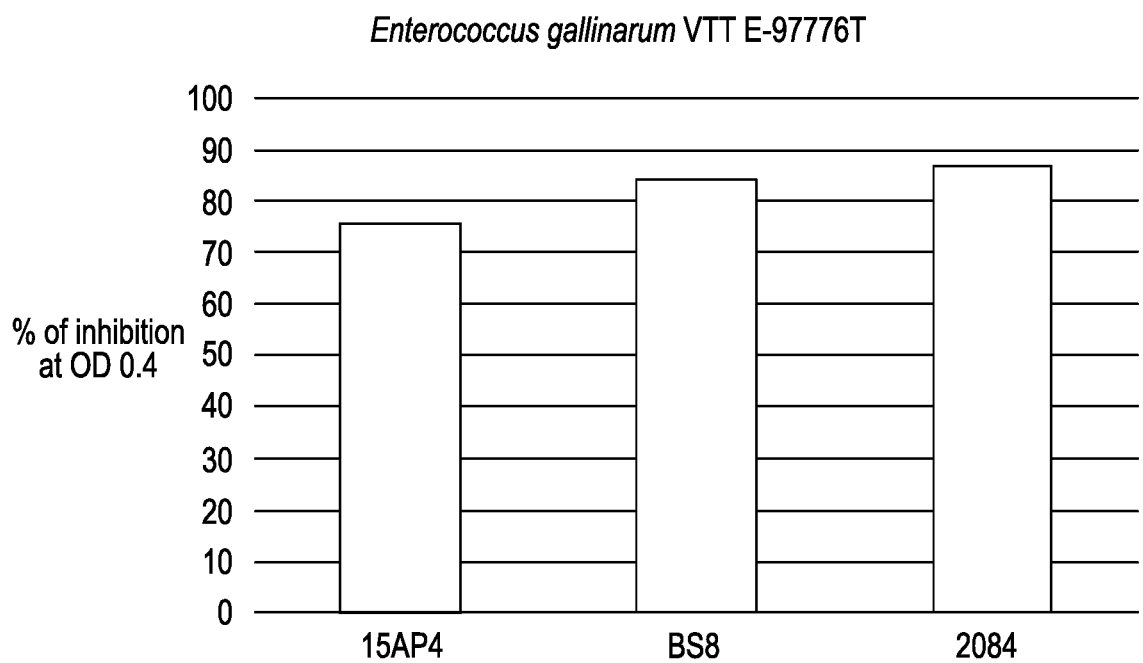
FIG. 5 shows the antimicrobial activity of the CFSs of B. amyloliquefaciens subsp. plantarum 15AP4, BS8 and 2084 against Enterococcus gallinarum VTT E-97776T expressed as % of inhibition at the exact end-point when the control pathogen curve reaches OD 0.4.

FIG. 5 shows the antimicrobial activity of the CFSs of *B. amyloliquefaciens* subsp. *plantarum* 15AP4, BS8 and 2084 (*Bacillus*-based component) against *Enterococcus gallinarum* VTT E-97776T expressed as % of inhibition at the exact end-point when the control pathogen curve reaches OD 0.4

Previous work has shown that broilers develop sepsis between weeks 1-3 in production as is seen in both outright inhibition and delays in the *E. cecorum* hitting the exponential growth phase. Supplementation of poultry feed with the *Bacillus*-based DFM(s) described herein may delay gut colonization, adherence and subsequent invasion, meaning that birds make it to slaughter with reduced incidence of clinical symptoms.

These data are quite compelling in comparison to the inhibition ranges of other pathogens that have been tested. The effect also seems quite consistent across the range of *E. cecorum* isolates tested, despite a natural variation in *Bacillus* efficacy.

The in vitro results presented herein demonstrate that supplementation of poultry feed with a *Bacillus*-based component described herein may be very effective in inhibiting or delaying all or part of the growth of the emerging pathogen, *E. cecorum* as well as inhibiting or delaying the growth of *Enterococcus* spp. in animals (as demonstrated in FIG. 5).

Example 3

Bacillus-Based Components for Inhibiting or Delaying the Growth of Enterococuss spp. in Animals A type strain is defined in the "International Code of Nomenclature of Bacteria" as the "nomenclatural type of the species", and is the "reference point" to which all other strains are compared to determine whether they belong to that species. Inclusion of the type strains of each of the bacterial species (see Table 6 below) included in this study enables a comparison of the inhibitory potential of strains characterized as "probiotic" versus strains belonging to the same species but not characterized as "probiotic". The hypothesis here is that probiotic properties are unique to specific strains and those properties cannot be transferred to any other strains belonging to the same species. Only those strains which have been thoroughly characterized and evaluated can be designated as "probiotic". The type strains included in this experiment are representative of the three distinct Bacillus species related to the strains studied here. Their origin and a non-exhaustive list of equivalent strains available in other culture collections are presented in Table 6.

TABLE 6

Type strains used in this study, their origin and non-exhaustive list of equivalences in other culture collections (adapted from Verslyppe et al., 2014; http://www.straininfo.net/)

| Bacterial species | Bacillus amyloliquefaciens | Bacillus subtilis | Bacillus licheniformis |
|---|---|---|---|
| Type strains used in this study | B. amyloliquefaciens DSM7T | B. subtilis DSM10T | B. licheniformis DSM13T |
| Origin of the type strains used in this study | DSMZ-Germany | DSMZ-Germany | DSMZ-Germany |
| ATCC American Type Culture Collection U.S.A. | | ATCC $6051^T$ | ATCC $14580^T$ |
| BCRC Bioresource Collection and Research Center Taiwan | BCRC 11601 | BCRC $10255^T$ | BCRC $11702^T$ |
| VTT Culture Collection Finland | VTT E-$80124^T$ | VTT E-$97009^T$ | VTT E-$95571^T$ |
| NBRC Biological Resource Center Japan | NBRC $15535^T$ | NBRC $12210^T$; NBRC $13719^T$; NBRC $16412^T$ | NBRC $12200^T$ |
| NCIMB National Collections of Industrial Food and Marine Bacteria U.K. | NCIMB $12077^T$ | NCIMB $3610^T$ | NCIMB $50016^T$; NCIMB $9375^T$ |
| NRRL Agricultural Research Service Culture Collection U.S.A. | NRRL B-$14393^T$ | NRRL B-$4219^T$ | NRRL NRS-$1264^T$ |
| LMG Belgian Coordinated Collections of Microorganisms/LMG Bacteria Collection | LMG $12234^T$ | LMG $7135^T$ | LMG $12363^T$; LMG $12407^T$; LMG $6933^T$ |
| CCUG Culture Collection, University of Goteborg Sweden | | CUCG $163B^T$ | CCUG $7422^T$ |
| CIP Collection de L'Institut Pasteur France | | CIP $52.65^T$; CIP $5265^T$ | CIP $52.71^T$ |
| KCTC Korean Collection for Type Cultures Korea (Rep. of) | | KCTC $3555^T$ | KCTC $1753^T$ |

The antimicrobial activity of those three type strains was evaluated against a set of 10 isolates of Enterococcus cecorum (Table 7) as described previously.

TABLE 7

Characteristics of the clinical isolates of Enterococcus cecorum originated from the poultry production used in this study.

| Geographic market | Topic | Strain Number | Origin of the isolate | Biological Origin | Date of Isolation | Collection |
|---|---|---|---|---|---|---|
| NAM[1] | Clinical disease | 12147-1 | Mountaire, NC | Spinal abscess | (May 23 2013) | WAU_US |
| NAM | Clinical disease | 12696M-1 | Mountaire, NC | Spinal Abscess | (Dec. 09, 2013) | WAU_US |
| NAM | Clinical disease | 11951-1 | Mountaire, NC | Spinal abscess Swab | (May 10, 2013) | WAU_US |
| NAM | Clinical disease | 11957-3 | Mountaire, NC | Spinal abscess Swab | (May 10, 2013) | WAU_US |
| EU[2] | Clinical disease | C.34.19 | BE[3] | bone marrow broiler | May 08, 2013 | Poulpharm_BE |
| EU | Clinical disease | D.42.11 | BE | Joint-production | Nov. 28, 2013 | Poulpharm_BE |
| EU | Clinical disease | E.59.56 | BE | femoral head-breeder | Oct. 09, 2014 | Poulpharm_BE |
| EU | Clinical disease | F.68.19 | BE | Joint - production | Dec. 01, 2015 | Poulpharm_BE |

TABLE 7-continued

Characteristics of the clinical isolates of *Enterococcus cecorum* originated from the poultry production used in this study.

| Geographic market | Topic | Strain Number | Origin of the isolate | Biological Origin | Date of Isolation | Collection |
|---|---|---|---|---|---|---|
| EU | Clinical disease | G.75.17 | BE | Articulation broiler production | Apr. 05, 2015 | Poulpharm_BE |

[1] = North America
[2] = Europe
[3] = Belgium

The percentages of inhibition of the growth of ten pathogenic *Enterococcus cecorum* isolates by each of the CFS obtained from the 3 distinct type strains are presented in FIG. 7. Unlike the 3 *B. amyloliquefaciens* strains from Enviva Pro (15AP4; BS8 and 2084) (see Table 4 above), the type strain *B. amyloliquefaciens* DSM7T exhibited no antimicrobial activity against the tested pathogens (FIG. 7). In this experiment, the CFS from the *B. amyloliquefaciens* type strain (DSM7$^T$) promoted the growth of the pathogen and was not able to inhibit any of the tested pathogens. This finding supports the strain-specificity of the antimicrobial property. Probiotic claims for a specific strain results from a scientific screening approach aiming to identify that strain or strain among thousands of strains, exhibiting uniqueness and, thus, be capable of providing benefits for the host as well as economical value for.

Thus, it was surprising to note that the *B. licheniformis* DSM13$^T$ exhibited greater antimicrobial activity (68.58% in average) against the *E. cecorum* pathogenic isolates compared to the commercial probiotic *B. licheniformis* strains and #10/4 respectively 1.36% and −12.41% (Table 4). The type strain *B. subtilis* DSM10$^T$ exhibited a percentage of inhibition of 26% in average which was still greater when compared to the average percentage exhibited by the commercial probiotic *B. subtilis* strain #11/1 (−21%) (FIG. 7 and Table 4).

What is claimed is:

1. A method for inhibiting or delaying all or part of the growth of pathogenic *Enteroccocus cecorum* or *Enteroccocus gallinarum* in an animal which comprises administering an effective amount of at least one *Bacillus*-based component selected from the group consisting of: a *Bacillus*-based direct fed microbial comprising *Bacillus* strain 15A-P4 ATCC Accession No. PTA-6507, a supernatant obtained from a *Bacillus* strain 15A-P4 ATCC Accession No. PTA-6507 culture or a combination thereof to an animal.

2. The method of claim 1 wherein the *Bacillus*-based direct fed microbial further comprises one or more of the following strains: *Bacillus* strain 2084 Accession No. NRR1 B-50013 and/or *Bacillus* strain LSSAO1 Accession No. NRRL B-50104.

3. The method of claim 1 wherein the animal is a monogastric animal.

4. The method of claim 2 wherein the animal is a monogastric animal.

5. The method of claim 1 wherein the animal is a multigastric animal.

6. The method of claim 2 wherein the animal is a multigastric animal.

7. The method of claim 1 wherein the monogastric animal is poultry.

8. The method of claim 2 wherein the monogastric animal is poultry.

9. The method of claim 1 wherein the at least one *Bacillus*-based component is administered directly to an animal through animal feed whether in the feed or on top of the feed or in a liquid.

10. The method of claim 2 wherein the at least one *Bacillus*-based component is administered directly to an animal through animal feed whether in the feed or on top of the feed or in a liquid.

11. The method of claim 9 wherein the at least one *Bacillus*-based component is administered to the animal in a form selected from the group consisting of a feedstuff, a feed additive composition, a premix or in a liquid.

12. The method of claim 10 wherein the *Bacillus*-based component is administered to the animal in a form selected from the group consisting of a feedstuff, a feed additive composition, a premix or in in a liquid.

* * * * *